US009437646B2

(12) United States Patent
Sekiguchi et al.

(10) Patent No.: US 9,437,646 B2
(45) Date of Patent: Sep. 6, 2016

(54) DETECTING DEVICE, DETECTOR, AND IMAGING APPARATUS USING THE SAME

(71) Applicant: CANON KABUSHIKI KAISHA, Tokyo (JP)

(72) Inventors: Ryota Sekiguchi, Kawasaki (JP); Masahiro Okuda, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 708 days.

(21) Appl. No.: 13/742,195

(22) Filed: Jan. 15, 2013

(65) Prior Publication Data

US 2013/0188041 A1    Jul. 25, 2013

(30) Foreign Application Priority Data

Jan. 19, 2012  (JP) .................................. 2012-009335

(51) Int. Cl.
  *G01S 13/89*  (2006.01)
  *G01S 13/02*  (2006.01)
  (Continued)

(52) U.S. Cl.
  CPC ..... *H01L 27/14669* (2013.01); *G01N 21/3581* (2013.01); *G01S 7/032* (2013.01); *G01S 13/89* (2013.01); *G01S 7/024* (2013.01); *G01S 13/003* (2013.01); *G01S 13/0209* (2013.01); *H01Q 1/36* (2013.01)

(58) Field of Classification Search
  CPC ... H01L 27/14; H01L 27/144; H01L 27/146; H01L 27/14665; H01L 27/141669; H01Q 1/36; H01Q 1/362; H01Q 3/24; G01N 21/17; G01N 21/25; G01N 21/31; G01N 21/35; G01N 21/3581; G01N 22/00; G01S 7/02; G01S 7/024; G01S 7/03; G01S 7/032; G01S 13/02; G01S 13/0209; G01S 13/003; G01S 13/88; G01S 13/89
  USPC ......... 342/21, 22, 27, 82, 89, 175, 176, 179, 342/42, 44; 343/700 R, 703, 720, 741, 744, 343/745, 753, 754, 772, 776, 778, 793, 802, 343/810, 812, 815, 816, 850, 907, 909, 912, 343/700 MS; 333/103, 104; 324/76.11, 95, 324/600, 629, 633, 636; 455/73, 78, 79, 82; 250/330, 332, 336.1, 338.1
  See application file for complete search history.

(56) References Cited

U.S. PATENT DOCUMENTS 3,671,970 A  *  6/1972  Layton ........................ 343/744
3,678,414 A  *  7/1972  Hallford ...................... 333/104
(Continued)

FOREIGN PATENT DOCUMENTS

CN         2205014 Y     8/1995
CN       102113122 A     6/2011
(Continued)

*Primary Examiner* — Bernarr Gregory
(74) *Attorney, Agent, or Firm* — Canon U.S.A., Inc. IP Division

(57) ABSTRACT

A detecting device which detects electromagnetic waves includes an antenna configured to receive electromagnetic waves, and a plurality of semiconductor rectifying devices serially connected to the antenna, and connected in parallel to each other such that the polarity is aligned, so as to receive electromagnetic waves propagated from the antenna, wherein the plurality of semiconductor rectifying devices are each disposed at positions where the phase of electromagnetic waves propagated from the antenna is substantially the same phase.

20 Claims, 16 Drawing Sheets

(51) Int. Cl.
*H01L 27/146* (2006.01)
*G01N 21/3581* (2014.01)
*G01S 7/03* (2006.01)
*G01S 13/00* (2006.01)
*G01S 7/02* (2006.01)
*H01Q 1/36* (2006.01)

(56) References Cited

U.S. PATENT DOCUMENTS

| | | | | |
|---|---|---|---|---|
| 3,852,755 | A * | 12/1974 | Works et al. | 343/815 |
| 4,015,259 | A * | 3/1977 | Siverhus et al. | 342/44 |
| 4,157,550 | A * | 6/1979 | Reid et al. | 343/703 |
| 4,297,708 | A * | 10/1981 | Vidal | 343/754 |
| 4,302,734 | A * | 11/1981 | Frosch | H01Q 3/24 333/104 |
| 4,320,404 | A * | 3/1982 | Chekroun | 343/754 |
| 4,344,077 | A * | 8/1982 | Chekroun et al. | 343/754 |
| 4,447,815 | A * | 5/1984 | Chekroun et al. | 343/754 |
| 4,518,966 | A * | 5/1985 | Sadones | 343/754 |
| 4,531,126 | A * | 7/1985 | Sadones | 343/909 |
| 4,542,532 | A * | 9/1985 | McQuilkin | 455/78 |
| 4,806,944 | A * | 2/1989 | Jacomb-Hood | 343/745 |
| 4,896,033 | A * | 1/1990 | Gautier | 343/754 |
| 4,924,238 | A * | 5/1990 | Ploussios | 343/802 |
| 4,975,712 | A * | 12/1990 | Chen | 343/754 |
| 5,001,495 | A * | 3/1991 | Chekroun | 343/754 |
| 5,030,962 | A | 7/1991 | Rees | |
| 5,047,783 | A | 9/1991 | Hugenin | |
| 5,128,621 | A * | 7/1992 | Berthaud | G01N 22/00 324/636 |
| 5,148,182 | A * | 9/1992 | Gautier et al. | 343/754 |
| 5,170,140 | A * | 12/1992 | Lowe et al. | 343/778 |
| 5,266,963 | A * | 11/1993 | Carter | 343/850 |
| 5,321,414 | A * | 6/1994 | Alden et al. | 343/816 |
| 5,430,369 | A * | 7/1995 | Bolomey et al. | 324/95 |
| 5,574,471 | A * | 11/1996 | Sureau | 343/909 |
| 5,579,024 | A * | 11/1996 | Sureau | 343/909 |
| 5,621,423 | A * | 4/1997 | Sureau | 343/909 |
| 5,623,145 | A | 4/1997 | Nuss | |
| 6,137,996 | A * | 10/2000 | Baumann | H01Q 1/362 455/82 |
| 6,317,092 | B1 * | 11/2001 | de Schweinitz et al. | 343/753 |
| 7,068,234 | B2 * | 6/2006 | Sievenpiper | 343/745 |
| 7,245,269 | B2 * | 7/2007 | Sievenpiper et al. | 343/909 |
| 7,324,043 | B2 * | 1/2008 | Purden et al. | 342/175 |
| 7,358,497 | B1 * | 4/2008 | Boreman et al. | 250/332 |
| 7,456,803 | B1 * | 11/2008 | Sievenpiper | 343/909 |
| 7,507,979 | B2 | 3/2009 | Vetrovec et al. | |
| 7,605,767 | B2 * | 10/2009 | Lee et al. | 343/754 |
| 7,868,829 | B1 * | 1/2011 | Colburn et al. | 343/700 MS |
| 7,907,101 | B2 * | 3/2011 | Ratajczak et al. | 343/912 |
| 8,115,683 | B1 * | 2/2012 | Stefanakos et al. | 343/700 MS |
| 8,816,282 | B2 * | 8/2014 | Thiel et al. | 250/338.1 |
| 2007/0001895 | A1 | 1/2007 | Kolinko | |
| 2008/0017813 | A1 | 1/2008 | Vetrovec | |
| 2010/0301217 | A1 * | 12/2010 | Sertel et al. | 343/720 |

FOREIGN PATENT DOCUMENTS

| | | |
|---|---|---|
| EP | 0727671 A2 | 8/1996 |
| JP | 09-162424 A | 6/1997 |

* cited by examiner

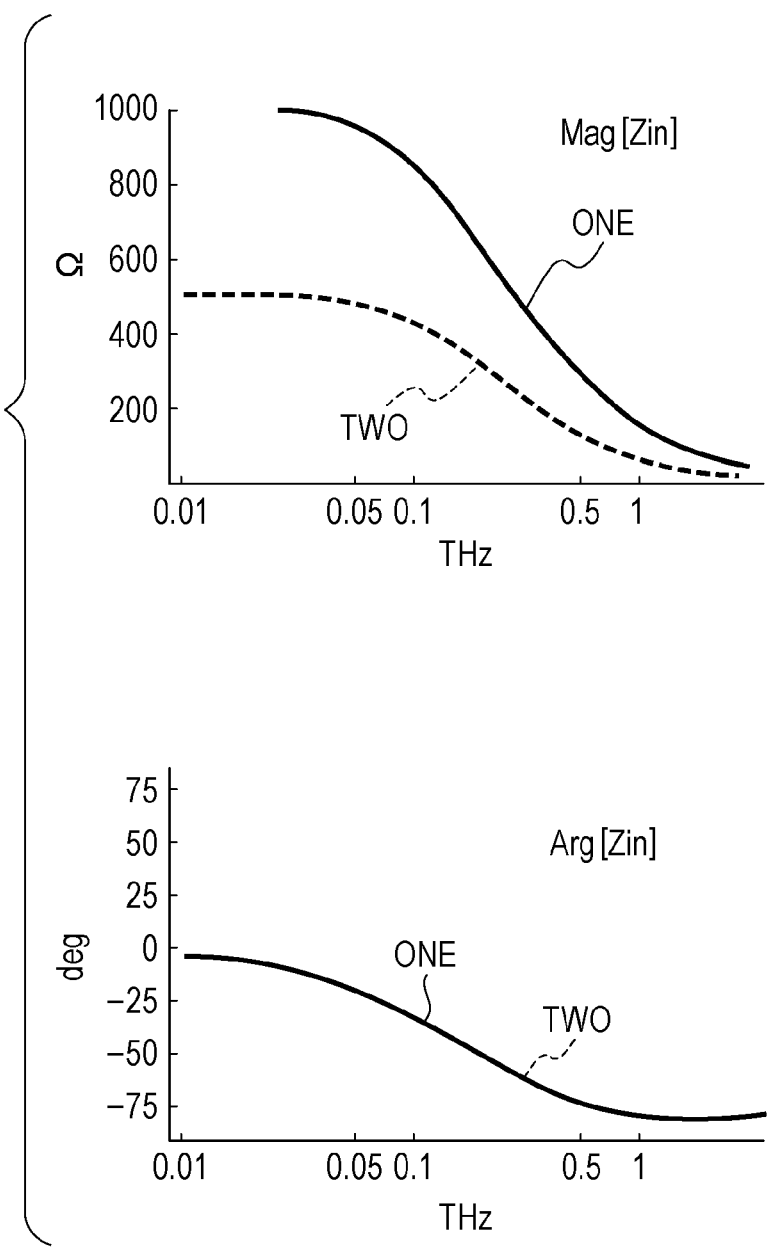

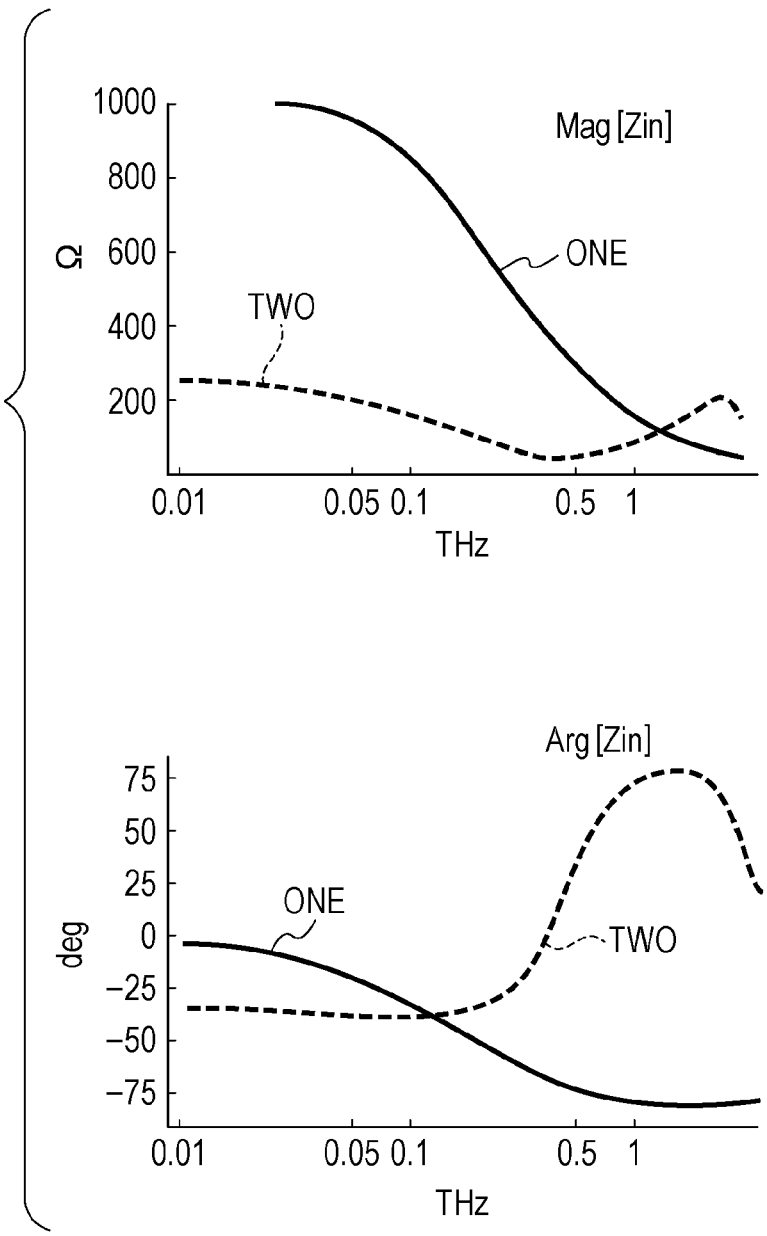

FIG. 11

|  | CUTOFF FREQUENCY | POWER EFFICIENCY (SN RATIO) | SERIES RESISTANCE DETECTING ELEMENT |
|---|---|---|---|
| CONVENTIONAL (ONE SBD) | 2 THz | 28% | Rs |
| FIRST EMBODIMENT (TWO SBDS) | 2 THz | 48% | Rs/2 |
| SECOND EMBODIMENT (n SBDS) | 2 THz | 48% OR GREATER | IDEALLY, APPROXIMATELY Rs/n TIMES |

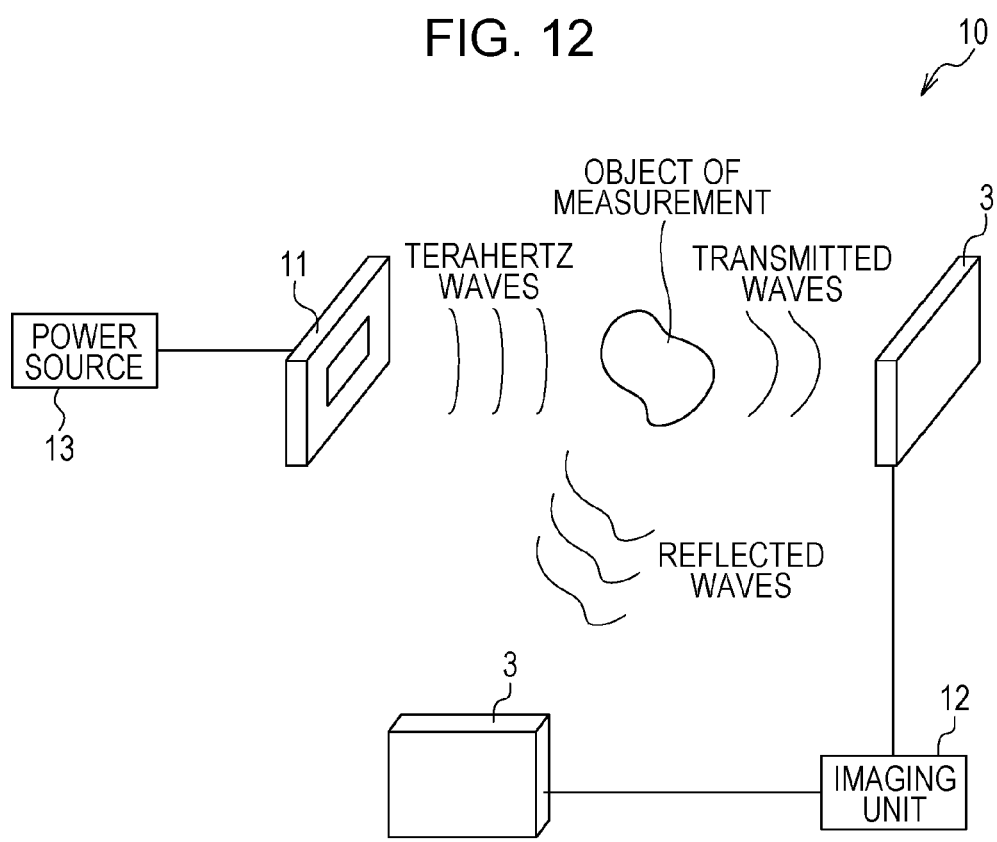

DETECTING DEVICE, DETECTOR, AND IMAGING APPARATUS USING THE SAME

BACKGROUND OF THE INVENTION

1. Field of the Invention

The present invention relates to a detecting device that detects electromagnetic waves, a detector, and an imaging apparatus that uses the detecting device and detector.

2. Description of the Related Art

As a detecting device that detects electromagnetic waves from millimeter wavebands (30 GHz to 300 GHz) to Terahertz bands (300 GHz to 30 THz), a thermal detecting device or a quantum detecting device has been used. A thermal detecting device may be a microbolometer that uses material such as a-Si, VOx, or the like, a pyroelectric element that uses material such as LiTaO3, TGS, or the like, and a Golay cell, or the like. Such a thermal detecting device is a device that can convert electromagnetic wave energy into heat energy, and detect changes in thermoelectric power. While a thermal detecting device does not necessarily have to have cooling, heat exchange is used, so response is relatively slow.

A quantum detecting device may be an intrinsic semiconductor device that uses a semiconductor having no accepter or donor doping (MCT, photoconductive device, etc.) or an extrinsic semiconductor device that uses a semiconductor to which an acceptor or donor has been added, or doped. Such a quantum detecting device is a device that captures the electromagnetic waves as photons, and detects the photovoltaic power or resistance changes from the semiconductor having a smaller band gap. While response is relatively fast, the heat energy from the ambient temperature cannot be ignored, and so cooling is needed.

Thus, recently, as a detecting device having a relatively fast response and that does not have to have cooling, a detecting device that detects electromagnetic waves from millimeter wavebands to Terahertz bands, using an antenna and semiconductor rectifying device, has been used. This detecting device captures electromagnetic waves as a high frequency signal, rectifies the high frequency signal received by an antenna or the like with a semiconductor rectifying device such as a Schottky barrier diode or the like, and detects the current flow at that time.

With a detecting device using an antenna and a semiconductor rectifying device such as a Schottky barrier diode or the like, the function of an RC low-pass filter is formed of junction capacity Cj in the Schottky barrier and serial resistance Rs. That is to say, high frequency components of the signal are cut off by the function of the RC low-pass filter, which then cannot be detected by the detecting device. Therefore, the cutoff frequency serving as the upper limit of the frequency band beyond which the detecting device cannot detect has to be higher than the frequency band of the electromagnetic wave to be detected.

Now, the junction capacity Cj that makes up the RC low-pass filter is proportional to the junction area of the Schottky electrode, which is the junction area of the semiconductor rectifying device, whereby as a method to increase the cutoff frequency $fc(=(2\pi \times RsCj)^{-1})$ of the detecting device, decreasing the junction area of the semiconductor rectifying device may be considered.

For example, performing simple calculations of the Schottky barrier diode and cutoff frequency, if the junction area of the Schottky electrode is microfabricated to 1 $\mu m^2$, then fc becomes approximately 300 GHz. If the junction area of the Schottky electrode is microfabricated to 0.1 $\mu m^2$ which is one-tenth thereof (approximately 0.3 $\mu m^2$ by when converted into terms of diameter), then fc becomes approximately 3 THz. Further, if the junction area of the Schottky electrode is microfabricated to 0.01 $\mu m^2$ which is one-tenth thereof (approximately 0.1 $\mu m^2$ when converted into terms of diameter), then fc can be estimated to be approximately 30 THz.

Japanese Patent Laid-Open No. 09-162424 discloses a detecting device that detects high frequency electromagnetic waves in this manner. According to Japanese Patent Laid-Open No. 09-162424, in detecting the high frequency electromagnetic waves, the junction area of a Schottky barrier diode which is a semiconductor rectifying device is microfabricated to 0.0007 $\mu m^2$, and an electromagnetic wave of approximately 28 THz from a $CO_2$ laser (wavelength 10.6 $\mu m$) is detected.

Thus, with a detecting device that detects electromagnetic waves using an antenna and semiconductor rectifying device as in the past, the junction area of the semiconductor rectifying device has been microfabricated in order to increase the cutoff frequency which is the frequency at the upper limit of the frequency band that can be detected. However, as the junction area of the semiconductor rectifying device decreases, the current flowing through the semiconductor rectifying device is limited, whereby the device resistance of the semiconductor rectifying device is increases. Particularly, in the case of a detecting device that detects electromagnetic waves of a 30 GHz to 30 THz frequency band, the device resistance results in at least several thousand $\Omega$.

SUMMARY OF THE INVENTION

The present invention provides a detecting device to detect electromagnetic waves with improved sensitivity, by reducing device resistance.

The present invention provides a detecting device which detects electromagnetic waves, including: an antennal configured to receive electromagnetic waves; and a plurality of semiconductor rectifying devices serially connected to the antenna, and connected in parallel to each other such that the polarity is aligned, so as to receive electromagnetic waves propagated from the antenna; wherein the plurality of semiconductor rectifying devices are each disposed at positions where the phase of electromagnetic waves propagated from the antenna is substantially the same phase.

The present invention also encompasses a detector and imaging apparatus. A detector according to the present invention to detect electromagnetic waves includes: the detecting device according to the present invention; and a measuring unit configured to measure an electric field at the antenna.

An imaging apparatus according to the present invention to perform image pickup of an object of measurement using electromagnetic waves includes: an oscillator configured to oscillate electromagnetic waves of a frequency band including a part of 30 GHz to 30 THz; the detector according to the present invention for detecting the electromagnetic waves; and an image constructing unit configured to construct an image relating to the object of measurement, based on electromagnetic waves detected by the detector.

According to the detecting device of the present invention, the device resistance of the overall detecting device is reduced, and accordingly electric power efficiency for detecting electromagnetic waves is increased, so the sensitivity of the detecting device is improved.

Further features of the present invention will become apparent from the following description of exemplary embodiments with reference to the attached drawings.

BRIEF DESCRIPTION OF THE DRAWINGS

FIGS. 3A through 3F are diagrams illustrating the disposal of a semiconductor rectifying device according to the first embodiment.

FIG. 11 is a diagram comparing a comparative example with the present invention.

FIG. 12 is a schematic diagram illustrating a schematic configuration of an imaging apparatus according to another embodiment.

DESCRIPTION OF THE EMBODIMENTS

Figure 1A:
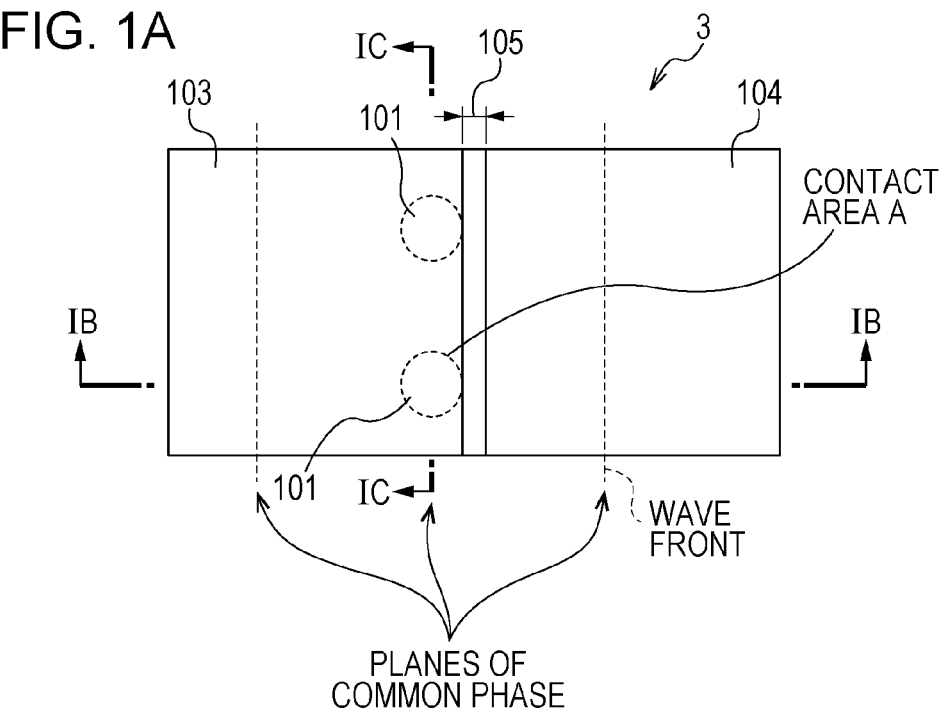
FIG. 1A is a perspective diagram illustrating a schematic configuration of a detecting device according to a first embodiment.

The detecting device according to the present invention relates to a detecting device that receives electromagnetic waves by a receiving antenna, and detects electromagnetic waves (oscillating electric field) that propagate over an antenna using a semiconductor rectifying device such as a Schottky barrier diode or the like.

With a detecting device that detects electromagnetic waves, the device resistance of the device in a semiconductor rectifying device increases itself. Thus, according to the present invention, it is preferable to dispose, as to an antenna, multiple semiconductor rectifying devices that are connected in parallel electrically and that have polarity thereof in the same direction, and configure later-described serial resistors Rs in parallel.

That is to say, the detecting device according to the present invention has an antenna that receives electromagnetic waves and multiple semiconductor rectifying devices, which are serially connected to the antenna and are connected so as to be mutually parallel with the polarity in the same direction, and which receive the electromagnetic waves propagated from the antenna. Also, the multiple semiconductor rectifying devices are each disposed in positions so that the phase of the electromagnetic waves (oscillating electric field) that propagated from the antenna is substantially the same phase. Thus, the combined resistance of the overall detecting device is lowered, and the sensitivity of the detecting device is improved.

Note that disposing the semiconductor rectifying devices with the same phase according to the present invention means that the semiconductor rectifying devices are each disposed in positions so that the phases of the electromagnetic waves propagated from the antenna are substantially the same phase. The positions for each of the multiple semiconductor rectifying devices to be disposed are not limited to positions where the absolute value of the phase difference of the propagated electromagnetic wave is 0, and positions having a phase difference within a predetermined range is allowable.

According to the detecting device of the present embodiment, positions having a phase difference in propagated electromagnetic waves of 0 or greater and $\pi/16$ are included as the same phase. Details of the disposal of the semiconductor rectifying devices will be described later.

Now, a semiconductor rectifying device may be a Schottky barrier diode, planar doped barrier diode (PDBD), PN (PIN) diode, Mott diode, backward diode, self-switching diode, and the like. Also, the semiconductor rectifying device may be used as a base-emitter configuration in a transistor or a gate-source configuration in a field-effect transistor (FET).

On the other hand, the antenna may be a dipole antenna, slot antenna, patch antenna, Cassegrain antenna, parabola antenna or the like. Also, the antenna is not restricted to planar antennas, and a stereo antenna may be used.

The present invention will now be described with reference to the drawings.

First Embodiment

The detecting device according to a first embodiment will be described with reference to FIG. 1.

Configuration of Detecting Device

Figure 1B:
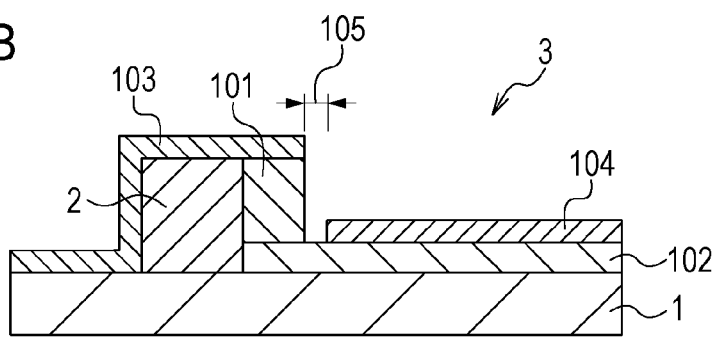
FIG. 1B is a diagram illustrating a cross-section of a detecting device according to the first embodiment.
Figure 1C:
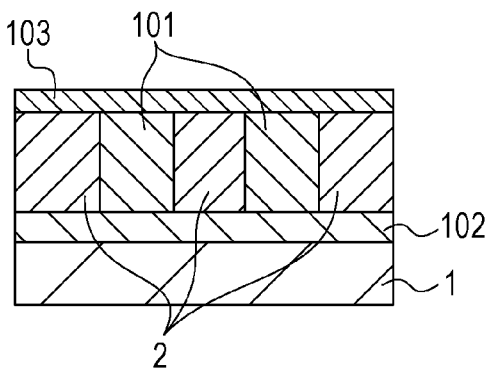
FIG. 1C is a diagram illustrating a cross-section of a detecting device that is parallel as to a plane of common phase of electromagnetic waves, according to the first embodiment.

FIG. 1A is a diagram illustrating a schematic configuration of a detecting device, where a portion is enlarged, according to the present embodiment. FIG. 1B is a diagram illustrating a cross-section of a detecting device according to the present embodiment, perpendicular as to planes of common phase of electromagnetic waves, taken along line IB in FIG. 1A. FIG. 1C is a diagram illustrating a cross-section of a detecting device according to the present embodiment, parallel as to planes of common phase of electromagnetic waves, taken along line IC in FIG. 1A.

A detecting device 3 according to the present embodiment has two semiconductor rectifying devices 101, and strip conductors 103 and 104 which are conductors made up of Al serving as antennas that propagate electromagnetic waves. Also, the detecting device 3 has a substrate 1, dielectric 2, and semiconductor layer 102. That is to say, at least one of the conductors making up the antenna and a semiconductor rectifying device are serially connected electrically via the semiconductor layer. FIGS. 1A through 1C illustrate a contact portion, where the semiconductor rectifying devices 101 and strip conductors 103 and 104 are contact, in an enlarged manner.

As illustrated in FIG. 1A, the detecting device 3 according to the present embodiment has two independent semiconductor rectifying devices 101, and are serially connected electrically so that the polarity of the strip conductors 103 and 104 which are antennas are facing the same direction. Also, the two semiconductor rectifying devices 101 are disposed so as to have the same phase as to the electromagnetic wave propagated from the strip conductors 103 and 104 which are antennas. This roughly equates to multiple semiconductor rectifying devices being disposed in positions where the phase of the electromagnetic wave propagated from the antenna is substantially the same phase.

Also, as illustrated in FIGS. 1B and 1C, the semiconductor rectifying device 101 is in contact with the strip conductor 103 which is a portion of the antenna. That is to say, the antenna is made up of a pair of conductors, and multiple semiconductor rectifying devices are arrayed in parallel touching one conductor of the pair. The shape of the semiconductor rectifying device 101 according to the present embodiment is a uniform cylinder, and the periphery of the semiconductor rectifying device 101 is surrounded by a dielectric 2. The multiple semiconductor rectifying devices each have a cylindrical form where a junction making up the semiconductor rectifying device is surrounded by a dielectric.

The multiple semiconductor rectifying devices are configured such that the areas of the cross-section perpendicular to the direction of current flowing at the junction making up the semiconductor rectifying devices are mutually equal. The dielectric 2 has a significantly higher resistance as to the propagated electromagnetic waves, as compared to the semiconductor rectifying device 101. Also, the semiconductor device 101 is also in contact with the semiconductor layer 102. Thus, the two strip conductors 103 and 104 are in ohmic contact electrically via the semiconductor rectifying device 101 and semiconductor layer 102.

The area of the junction of the semiconductor rectifying device 101 of the detecting device 3, in order to detect electromagnetic waves of a frequency band of 30 GHz to 30 THz, has a minute area that is 10 $\mu m^2$ or less. The area of the junction here is as described above. The junction of the strip conductor 103 and semiconductor device 101 can be considered to be junction area A. Also, if the semiconductor rectifying device uses PDBD or a transistor, the area indicates the junction area on a mesa.

As to the junction area A of the semiconductor rectifying device, 1 $\mu m^2$ or less is preferable if the material of the semiconductor rectifying device uses silicon. Also, a junction area A of 10 $\mu m^2$ or less is preferable if, of compound semiconductor materials with a relatively high mobility, a Group III-V semiconductor material such as GaAs is used. This is because the junction capacity Cj of the semiconductor rectifying device 101 is determined from the typical junction thickness in a Schottky barrier diode being approximately 10 to 100 nm and the relative permittivity being approximately 10. Also, the serial resistance Rs of the semiconductor rectifying device 101 depends on the mobility of the material, but on minutely small areas as described above, reducing to around 100Ω is difficult.

Now, the junction area of the semiconductor rectifying devices herein is near the precision limitation of photolithography such as a stepper or aligner. Therefore, a gap 105 that approximates the precision limitation in manufacturing occurs between the semiconductor rectifying device 101 and the strip conductor 104.

Thus, according to the present embodiment, the gap 105 is filled in with a semiconductor layer 102 having an electrical conductivity lower than the strip conductor 104, as needed, between the semiconductor rectifying device 101 and strip conductor 104. Thus, the semiconductor rectifying device 101 and strip conductor 104 are in ohmic contact electrically via the semiconductor layer 102. Also, the main factor of the serial resistor Rs which is the resistance component from the semiconductor rectifying device 101 to the strip conductor 104 is the resistance of the semiconductor layer 102.

The equivalent circuit of the detecting device 3 in the configuration described above with reference to FIG. 1 will be described below, having the junction area at the Schottky junction between the semiconductor rectifying device 101 and strip conductor 103 as A.

Equivalent Circuit of Detecting Device

Figure 2:
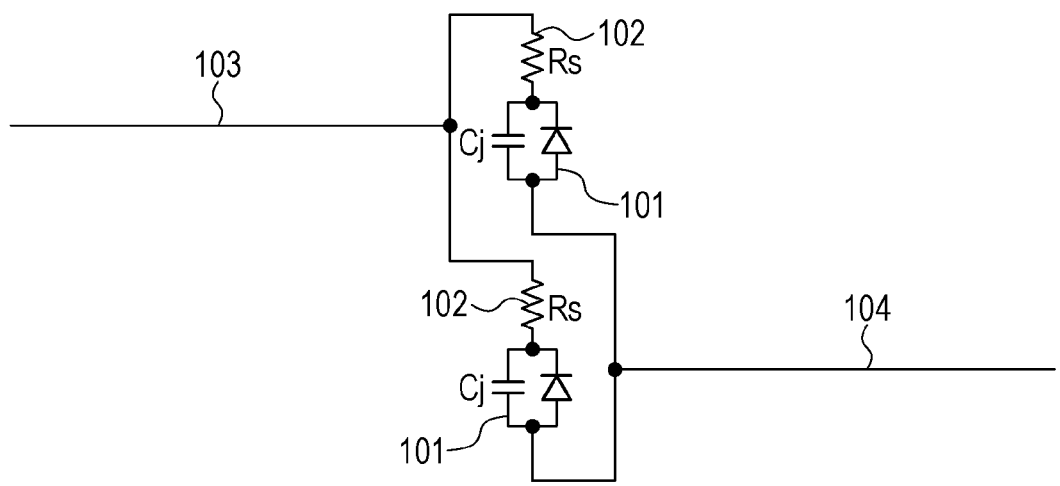
FIG. 2 is a diagram illustrating an equivalent circuit of a detecting device according to the first embodiment.
Figure 3B:
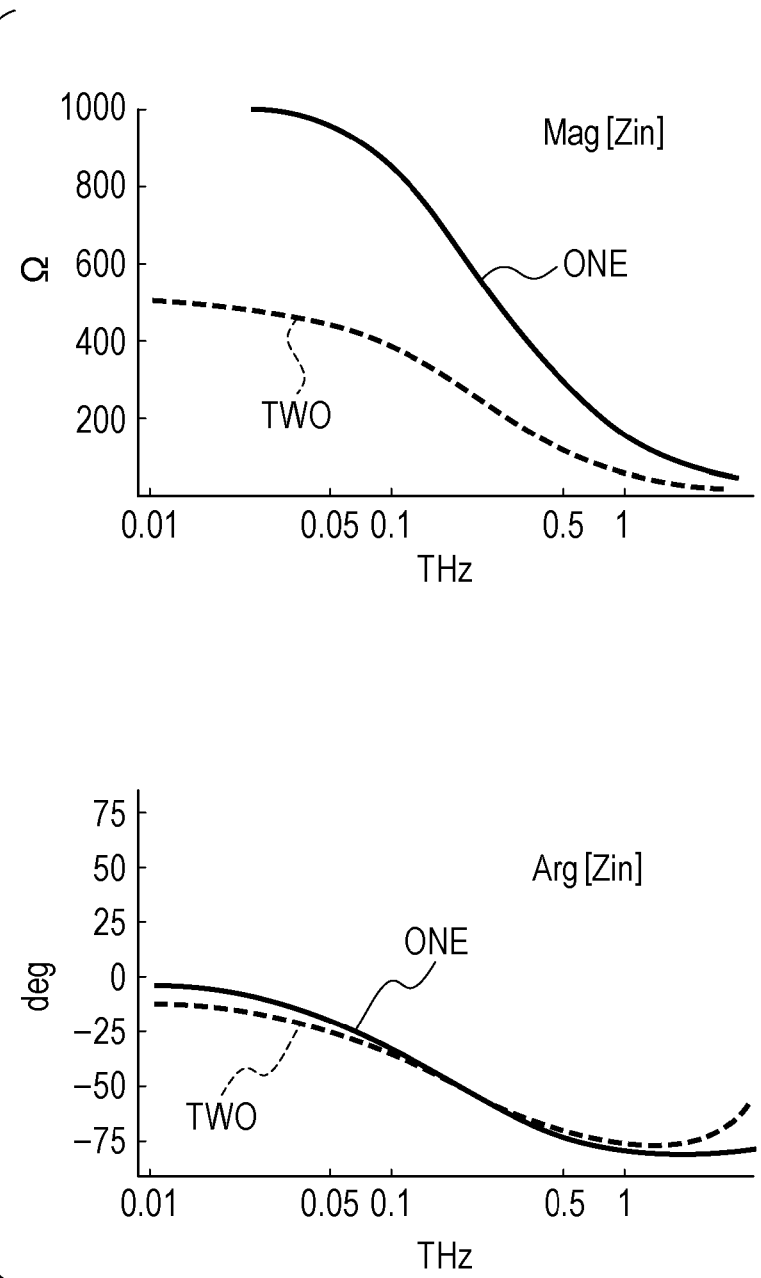
Figure 3C:
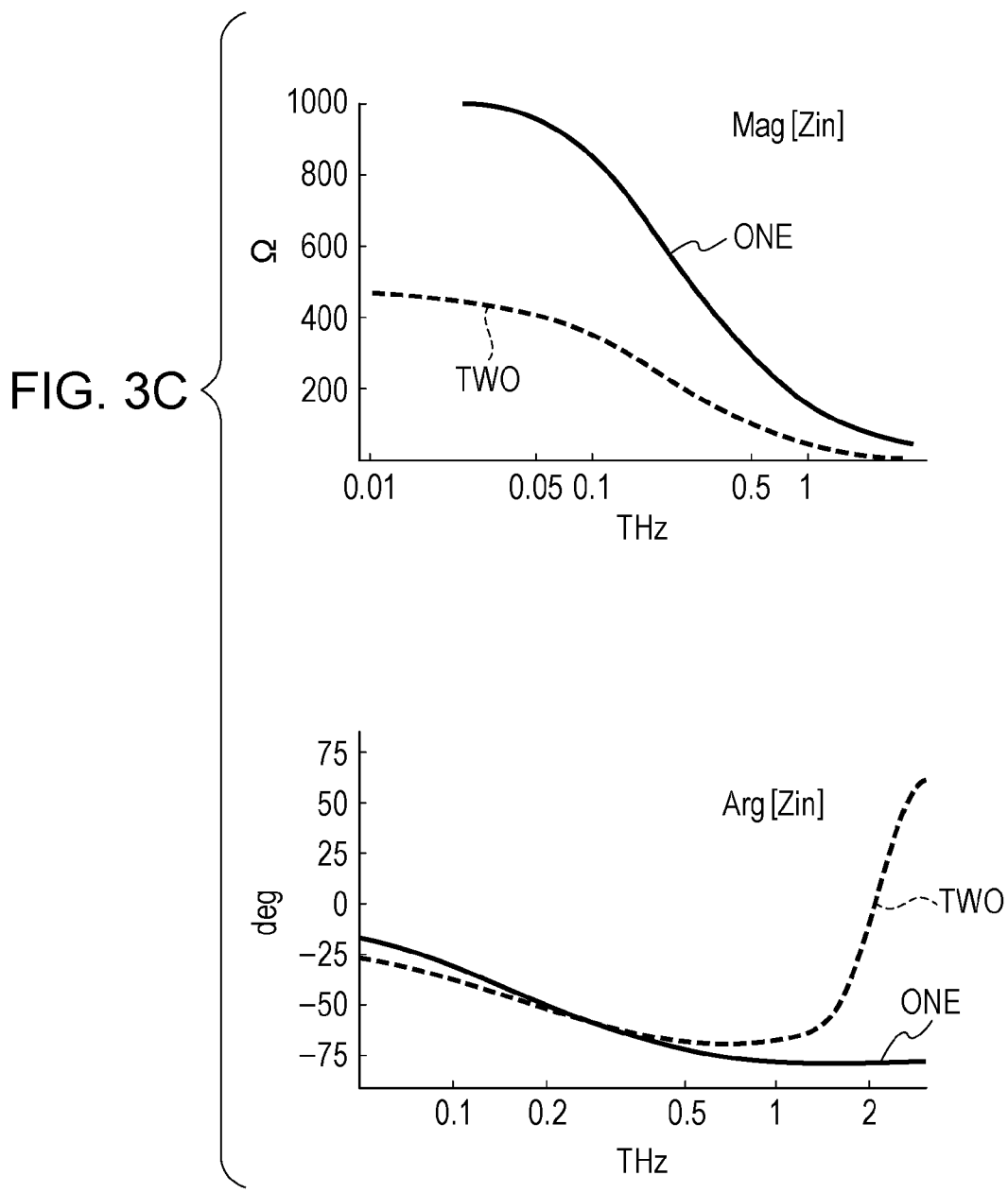
Figure 3D:
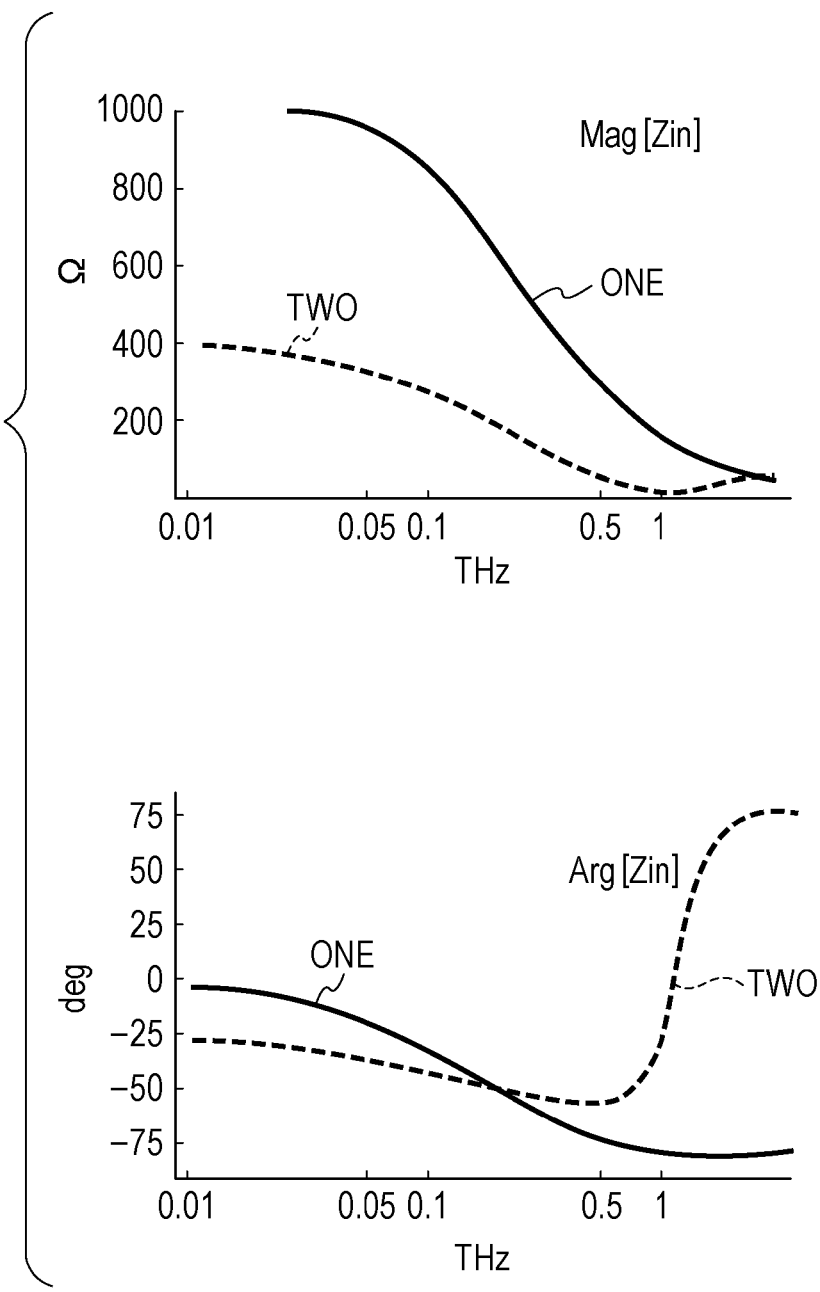
Figure 3F:
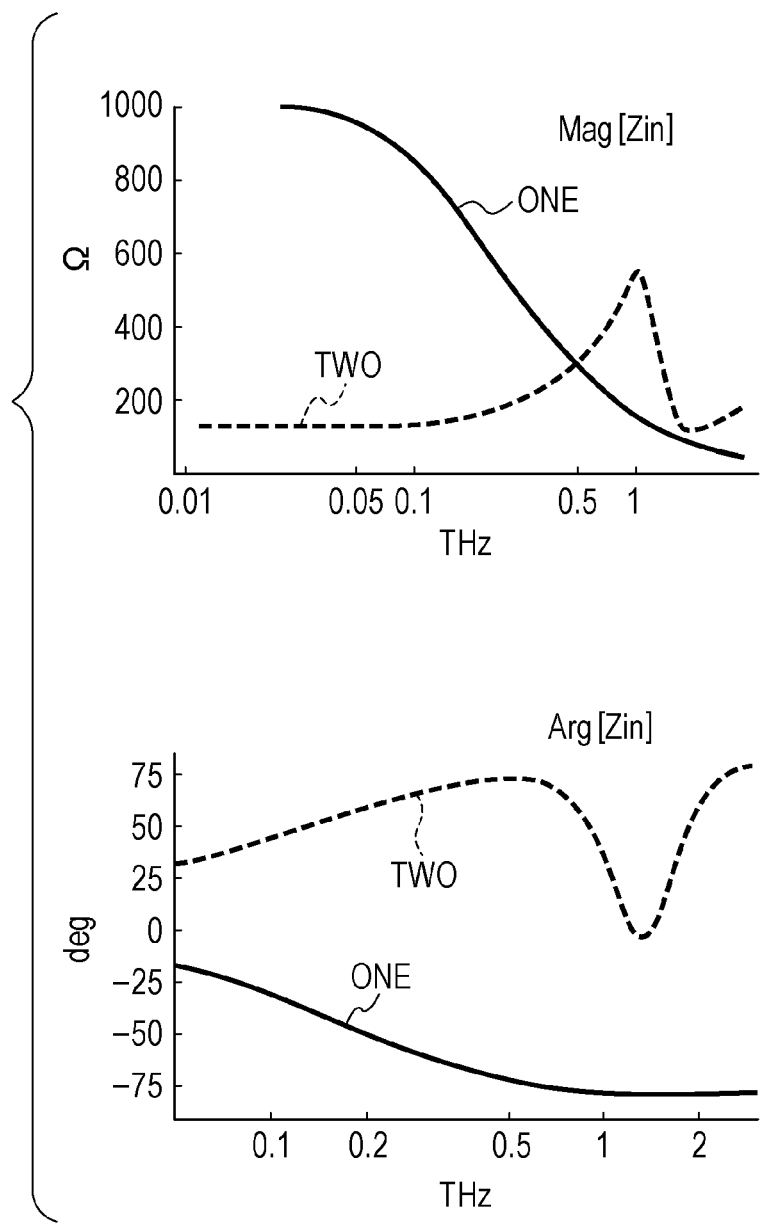

FIG. 2 is a diagram illustrating an equivalent circuit of a detecting device according to the present embodiment. However, for simplification here, the circuit is assumed to be configured only with a serial resistor Rs which is a resistor combining the semiconductor rectifying device 101 and semiconductor layer 102 or the like, and a junction capacity Cj of the semiconductor rectifying device. That is to say, this can be viewed as a resistor-capacitor circuit (RC circuit) made up of the junction capacity Cj of the Schottky barrier diode 101 and the serial resistor Rs, i.e. an RC low-pass filter.

The cutoff frequency fc, which is a frequency in the upper limit of the frequency band that can be detected by the detecting device, is found as $fc=(2\pi \times RsCj)^{-1}$. Now, the serial resistor Rs between the Schottky barrier diode 101 and strip conductor 104 can be viewed as being approximately the same as the resistor of the semiconductor layer 102, and is inversely proportional to $\sqrt{A}$ at the junction area A between the Schottky barrier diode 101 and strip conductor 103. On the other hand, the junction capacity Cj which the Schottky barrier diode 101 is seen as having, ideally is proportional to A.

In other words, in the case of making up an RC circuit using one of the semiconductor rectifying devices 101 of the junction area A, $RsCj \propto \sqrt{A}$ holds, whereby the cutoff frequency fc has the relation of $fc=(2\pi \times RsCj)^{-1} \propto 1/\sqrt{A}$.

Now, in order to reduce the combined impedance of the detecting device and improving the detection sensitivity, the serial resistor Rs has to be reduced, and as a method thereto, increasing the junction area A of the semiconductor rectifying device 101 may be considered. However, if the junction area A of one of the semiconductor rectifying devices 101 is increased to twice the size, for example, the above-described cutoff frequency fc: $fc=(2\pi \times RsCj)^{-1}$ becomes $1/\sqrt{2}$, and is decreased. That is to say, the frequency band of the electromagnetic waves that can be detected is unfortunately reduced.

The detecting device 3 according to the present embodiment has two mutually independent semiconductor rectifying devices 101 of the junction area A, whereby reduction of the frequency band can be suppressed and combined impedance of the detecting device can be reduced. That is to say, the detection sensitivity of detecting can be improved as compared to a detecting device used in the past that uses one semiconductor rectifying device 101. Further details will be described below.

The detecting device 3 according to the present embodiment has two semiconductor rectifying devices 101, which are disposed so that the phases of the electromagnetic waves propagated (transmitted) to the semiconductor rectifying devices 101 are the same phase, and the two semiconductor rectifying devices 101 are serially connected electrically and the polarity thereof are facing the same direction as to the propagated electromagnetic waves.

With such a detecting device 3, as can be seen from FIG. 2, the two serial resistors Rs are also serially connected and distributed, whereby in the case of combining resistance for the overall detecting device, the resistance becomes Rs/2. Also, the semiconductor rectifying devices 101 are disposed so as to have the polarity thereof face the same direction, whereby the overall junction area is 2A, and the overall junction capacity is 2 Cj.

Accordingly, compared to a detecting device used in the past that uses one semiconductor rectifying device 101, the overall detecting device according to the present embodiment has a serial resistor Rs that is ½ times the size and a junction capacity Cj that is double. Therefore, if we fit the detecting device according to the present embodiment into the cutoff frequency fc equation, $fc=(2\pi \times (Rs/2)2Cj)^{-1}$ holds, and the cutoff frequency is not reduced as compared to the detecting device used in the past which uses only one semiconductor rectifying device.

Now, the electromagnetic wave is propagated to the semiconductor rectifying device 101 positioned in the center from the strip conductor 103 on the left of the diagram or the strip conductor 104 on the right. Accordingly, the semiconductor rectifying device 101 is positioned at the same phase as to the electromagnetic wave propagating over the strip conductor, whereby two semiconductor rectifying devices 101 are disposed so as to be parallel as to the same wave face of the electromagnetic wave. That is to say, as illustrated in FIG. 1, two semiconductor rectifying devices 101 are connected to the antenna so as to be parallel as to planes of a common phase of the electromagnetic wave and disposed, so that the electromagnetic waves rectified by each of the two semiconductor rectifying devices 101 have the same wave front, i.e. the phase difference=0.

With the above-described configuration, the cutoff frequency of the detecting device 3 being reduced can be suppressed, and also the device resistance of the entire detecting device as to the detected electromagnetic wave (combined resistance) can be reduced by half. Thus, by reducing the device resistance of the entire detecting device, mismatching of resistance with an antenna having a comparatively small resistance value can be reduced.

Now, the disposal of the two Schottky barrier diodes used as semiconductor rectifying devices 101 are set as "positions at the same phase" as to the propagated electromagnetic wave, but even if not in positions where the phase difference is strictly 0, the advantage of the present invention of improving detecting sensitivity can be obtained.

Therefore, a position at the same phase according to the present embodiment is not limited to disposal where the phase difference of electromagnetic waves propagated to each of multiple semiconductor rectifying devices is 0, and disposal having a phase difference within a predetermined range is allowable. Now, as described above, a position at the same phase is the position where the phases of the electromagnetic waves propagated from the antenna are substantially the same phase. Also, according to the present invention, the semiconductor rectifying devices are each disposed at these positions.

The disposal relation of the two Schottky barrier diodes will be described next. FIG. 3 is a diagram describing the disposal relation of the two Schottky barrier diodes. The diagram illustrates the device resistance of the detecting device (combined resistance) [Ω], and a phase angle Mag [Zin] of the electromagnetic waves propagating over the two Schottky barrier diodes, as to the frequency bands of the detected electromagnetic waves.

Simulations are made in the order of FIGS. 3A, 3B, 3C, 3D, 3E, and 3F, where the phase differences as to the electromagnetic waves are 0, $\pi/64$, $\pi/32$, $\pi/16$, $\pi/8$, and $\pi/4$, in the case of two Schottky barrier diodes being disposed (broken lines) as compared to the case of one being disposed (solid lines).

Now, we assume feature impedance as a strip conductor to be 300Ω. Also, as another numerical value example, a Schottky barrier diode is used where Cj=1 fF and serial resistor Rs=1000Ω. Also, as a roll-off frequency that includes all of the resistances of the detecting device, $fr=\sqrt{(1+Rs/Rd)}$ $(2\pi \times \sqrt{RsRd}Cj)^{-1}$, calculations are made using a frequency band of 1.6 THz or less.

Now, using two Schottky barrier diodes, when the phase differences are $\pi/4$ and $\pi/8$, the phase angles Arg[Zin] of the electromagnetic waves that are propagated over the two Schottky barrier diodes are separated. On the other hand, when $\pi/32$ and $\pi/64$, the phase angles Arg[Zin] gradually begin to match, and at $\pi/64$, are almost matched. Therefore, with a THz detector or the like for communication where phase angle becomes important, it is desirable for the disposal of the two semiconductor rectifying devices to be disposed so that the absolute value of the phase difference of the transmitted electromagnetic waves (oscillating electric field) is 0 or greater and $\pi/32$ or less.

Also, with $\pi/16$, $\pi/32$, and $\pi/64$, the impedance Mag[Zin] is half of when one Schottky barrier diode is used, and is roughly an ideal value. Therefore, in the case of using for an imaging apparatus or the like where phase angle does not have to be considered, it is more desirable for the two Schottky barrier diodes to be disposed so that the transmitted electromagnetic waves have a phase difference of 0 or greater and $\pi/16$ or less. That is to say, the combined impedance and the range of same phases from the perspective of a phase angle are determined according to the use situation of the detecting device.

Now, an optimal detecting wavelength is generally 32 to $(\pi/16)/2\pi$ times the square root of the junction area thereof or more. Therefore, it is preferable for a detector according to the present embodiment to detect a frequency band from a millimeter waveband having a wavelength of 10 μm or greater to a terahertz band, where disposal of the Schottky barrier diodes are such that the phase difference is $\pi/16$ or less is easy.

Also, it is desirable for a portion of the strip conductor touching the Schottky barrier diodes 101 to be flat so that the phase and wave front of the electromagnetic waves of the strip conductors 103 and 104 (e.g., equipotential plane) can be defined. Also, Schottky barrier diodes having the same junction area A are used, but this is not restrictive, and Schottky barrier diodes each having different junction areas may also be used. Further, configuring the detecting device using the same semiconductor rectifying devices is not restrictive, and semiconductor rectifying devices of different types or dimensions may be used.

Second Embodiment

Whereas two semiconductor rectifying devices are illustrated in the first embodiment, the present embodiment has n(n≥3) semiconductor rectifying devices such as Schottky barrier diodes or the like disposed in a row. The other configurations are the same as in the first embodiment, so descriptions of similar configurations will be omitted.

Figure 4A:
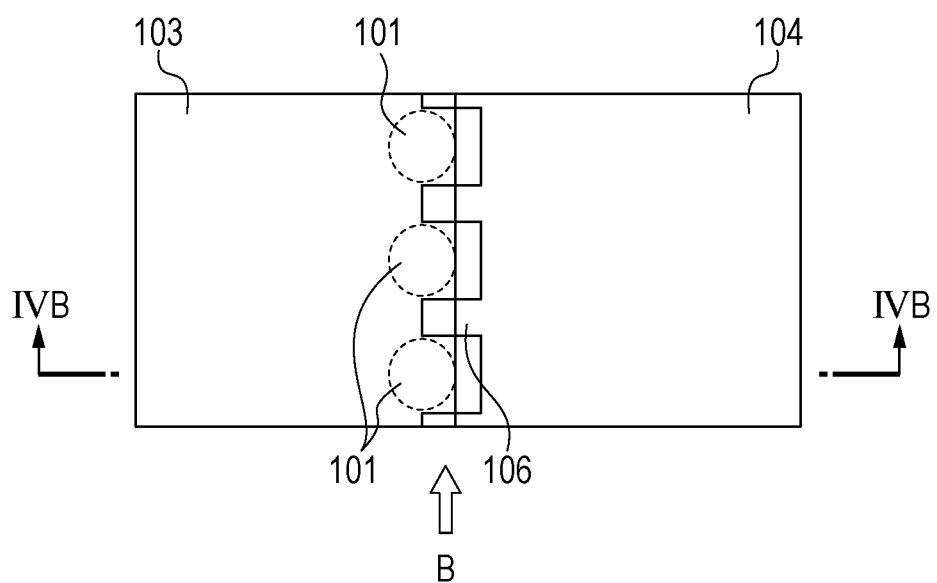
FIG. 4A is a diagram illustrating a configuration of a detecting device according to a second embodiment.
Figure 4B:
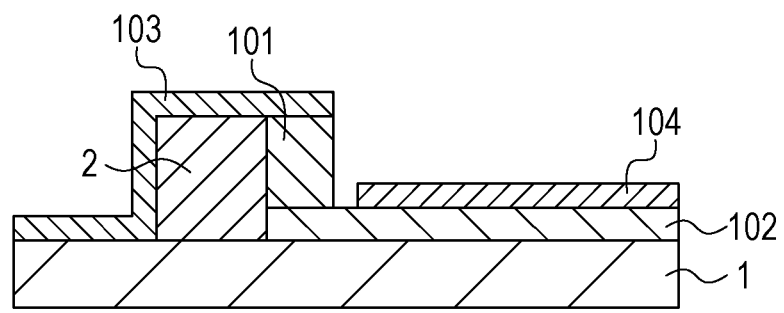
FIG. 4B is a diagram illustrating a cross-section of a detecting device according to the second embodiment.

A detecting device 3 according to the present embodiment will be described below. FIG. 4A is a schematic diagram illustrating a detecting device according to the present embodiment. FIG. 4B is a diagram illustrating a cross-section of the detecting device that is vertical as to a plane of the same phase, according to the present embodiment.

Note that the present embodiment exemplifies a case of having three semiconductor rectifying devices 101, but is not limited to three. There may be three semiconductor rectifying devices 101, or the number may be expanded to 4, 5, . . . n. That is to say, the detecting device according to the present embodiment only has to have multiple semiconductor rectifying devices, and these may be disposed so that at least three of the semiconductor rectifying devices have the same phase as to the electromagnetic wave. Now, when having n semiconductor rectifying devices, the detecting device resistance is ideally 1/n times the resistance of when there is one semiconductor rectifying device, which is low resistance.

However, in the event of arraying multiple semiconductor rectifying devices, the parallelization efficiency of resistance with the present embodiment should be taken into consideration. Parallelization efficiency here approximates to the amount of resistance that is decreased when n semiconductor rectifying devices are connected in parallel, and the ideal parallelization efficiency is approximately 1/n times as compared to when the combined resistance of the overall detecting device is one.

However, depending on the disposal of the semiconductor rectifying devices, there are cases in which the ideal parallelization efficiency is not achieved. For example, let us assume a case with the first embodiment wherein, in a state of the semiconductor rectifying devices 101 being connected while surrounded by the strip conductor 104 in the vertical direction, as shown in FIG. 1A, a third device is added between the two semiconductor rectifying devices. In such an array, the resistance of the added semiconductor rectifying device increases, whereby the parallelization efficiency of the overall detecting device is reduced.

In order to suppress reduction of the parallelization efficiency, a salient portion 106 may be provided to the strip conductor 104. That is to say, a salient portion 106 that is in a salient shape formed to be positioned between the semiconductor rectifying devices may be provided to the edge portion positioned on the semiconductor rectifying device side of the strip conductor 104. The reason thereof is to have the same shortest distance between the strip conductor 104 and all of the semiconductor rectifying devices 101, whereby the serial resistance Rs is not increased when the distance to the semiconductor layer 102 is short, and reduction of parallelization efficiency can be suppressed.

Note that the shape of the salient portion 106 is not limited to a rectangular shape, and various shapes such as a triangle, half-circle, or the like may be used. In the case that the number of devices of the semiconductor rectifying devices 101 increases to three or four, disposing the salient portion 106 of the strip conductor 104 formed of a material having an electric conductivity higher than the semiconductor layer 102 between the devices of the semiconductor rectifying devices 101 is effective.

Note that the salient portion 106 of the present embodiment is also important in an arrayed device array such that the phase difference between the semiconductor rectifying devices is sufficient small. In this event, the salient portions may be disposed in a mesh form.

Also, according to the present embodiment, the configuration has multiple semiconductor rectifying devices connected to an antenna, but a configuration may have a transmission line that transmits electromagnetic waves connected to the antenna, enabling electromagnetic waves to be propagated to the semiconductor rectifying devices from the antenna via the transmission line.

Third Embodiment

Further details of the configuration of a detecting device 3 and a detector 4 having the detecting device 3 will be described below.

Configuration of Overall Detector

Figure 5A:
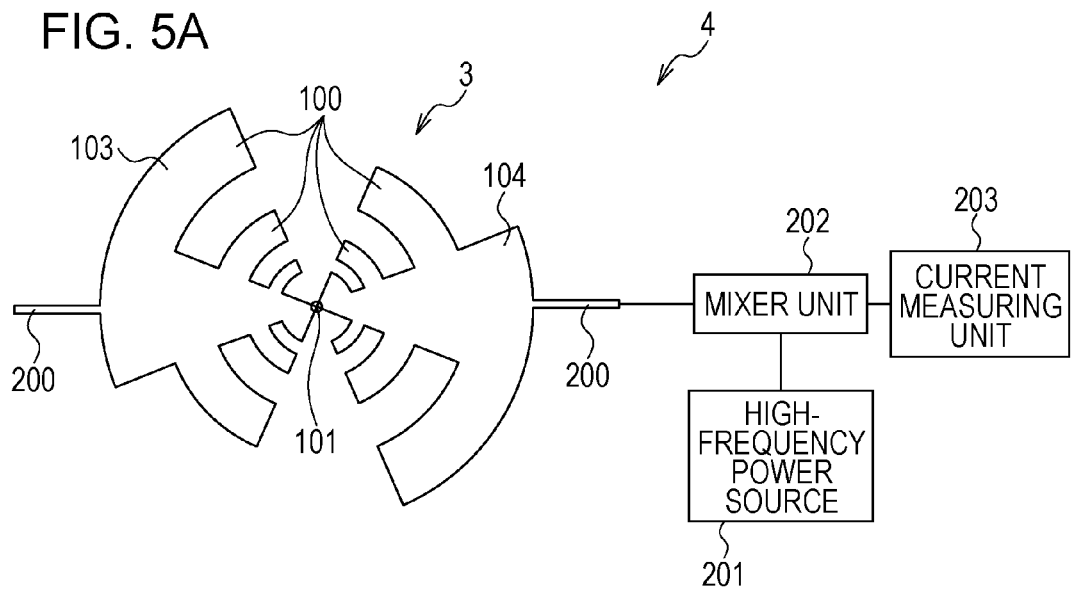
FIG. 5A is a diagram illustrating a configuration of a detector according to a third embodiment.
Figure 5B:
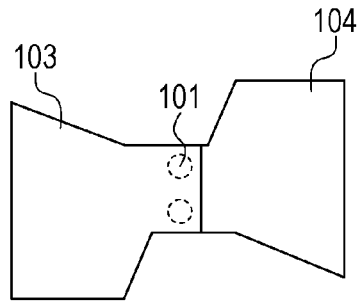
FIG. 5B is a diagram illustrating an enlarged view of the center portion of a detecting device according to the third embodiment.
Figure 5C:
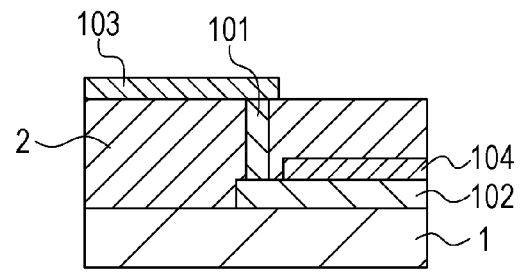
FIG. 5C is a diagram illustrating a cross-section of a detecting device according to the third embodiment.

The detector 4 according to the present embodiment will be described with reference to FIGS. 5A through 5C. A Schottky barrier diode 101 is used as a semiconductor rectifying device. FIG. 5A is a perspective view of a detector according to the present embodiment. FIG. 5B is a diagram enlarging the center portion of the detector according to the present embodiment. FIG. 5C is a diagram illustrating a cross-section of the detector according to the present embodiment.

As illustrated in FIG. 5A, the detector has a log periodic antenna serving as an antenna 100 that receives and transmits electromagnetic waves. The band received on the log periodic antenna is a wide band, and electromagnetic waves of various frequencies can be received on one antenna. The antenna 100 according to the present embodiment receives electromagnetic waves in frequency bands from 0.2 THz to 2.5 THz.

Now, the antenna 100 is made up of strip conductors 103 and 104, which are two non-contact conductors disposed on a substrate. The dimensions of the antenna 100 are 250 μm for the radius (outer radius) from the center portion where the illustrated Schottky barrier diode is disposed to the outermost side, 10 mm for the radius (inner radius) to the innermost side, the number of teeth having log period 0.7 is nine, and the angle of the teeth is 45 degrees.

As illustrated in FIGS. 5B and 5C, according to the present embodiment, two mesa-shaped Schottky barrier diodes are disposed in the center portion of the strip conductors 103 and 104 so as to have a plane of common phase of the electromagnetic waves. The Schottky barrier diodes 101 are embedded in a oxide film or the like, and connected with the strip conductor 103 that approximates a Schottky electrode. Also, the Schottky barrier diodes 101 are configured to be connected to the strip conductor 104 which approximates an ohmic electrode via the semiconductor layer 102 which is a high density carrier layer.

The detecting device 3 with this type of configuration first forms a n+ layer with a carrier density of $10^{19}$ cm$^{-3}$ and a n layer of $10^{18}$ cm$^{-3}$ on an Si substrate with a Fz (Floating Zone) method, using an epitaxial growth method.

Next, etching is performed on an epitaxial layer, following which a Schottky electrode is formed on the epitaxial layer by vapor-depositing a Schottky metal, thereby forming a Schottky barrier diode 101. Both dry etching and wet etching may be used.

Next, the strip conductor 104 made up of Al is formed, and passivation (Film protecting process to protect chip surface from contamination such as water, movable ions (ions that move freely and are not fixed) and increase device reliability. Generally used materials are nitride film and phosphosilicate glass (PSG)) by a $SiO_2$ dielectric 2 is performed.

Further, the SiO$_2$ is exposed to expose the Schottky barrier diode 101. Finally, the strip conductor 103 made up of Al is formed as a film, whereby the manufacturing of the detecting device according to the present embodiment is completed. Thus, the detecting device 3 according to the present embodiment can be readily manufactured using common semiconductor process techniques.

As to the configuration of the detecting device 3 according to the present embodiment, the diameter on the contact portion side of the strip conductor 103 and Schottky barrier diode 101 is set to 0.6 μm and the distance between the Schottky barrier diode 101 and strip conductor 104 is 1 μm, so that the cutoff frequency of the RC low-pass filter is approximately 3 THz. Also, the spacing between the two Schottky barrier diodes 101 is 2 μm.

Figure 10:
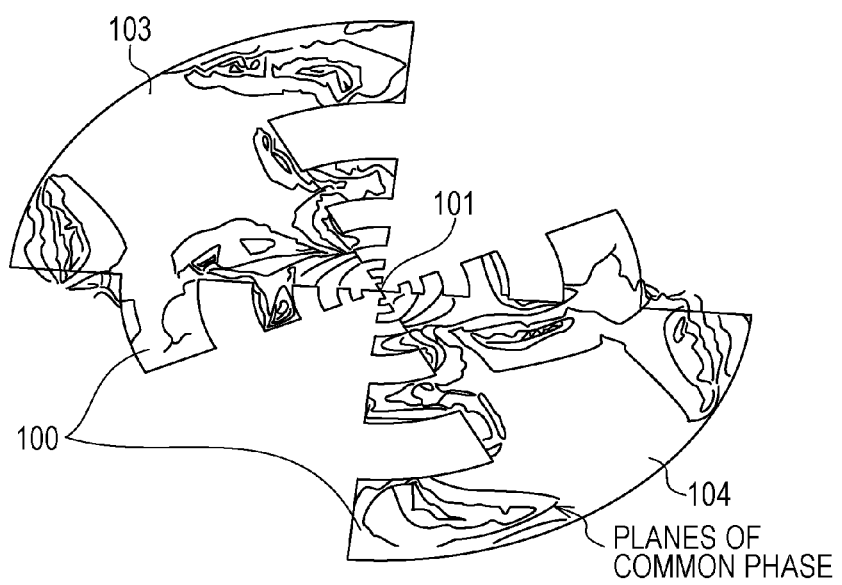
FIG. 10 is a diagram illustrating a phase of electromagnetic waves of the detecting device according to the third embodiment.

To confirm this, the results of a simulation of a 0.7 THz electromagnetic distribution are described in FIG. 10. FIG. 10 describes the results of simulating a plane of common phase of an antenna, whereby we can see that in the center area, wave fronts of electromagnetic waves that are approximately uniform with equal spacing (plane of common phase) are formed.

Now, the serial resistance Rs in the case of using one Schottky barrier diode according to the present embodiment is 1000Ω. Therefore, the combined resistance of the detecting device according to the present embodiment where two Schottky barrier diodes 101 are connected in parallel is approximately 500Ω.

Also, an estimation of the reflection from the Schottky barrier diodes can be found by a reflection coefficient Γ=(Ra−Rd)/(Ra+Rd). Ra is the resistance of the antenna, and Rd is the device resistance of the Schottky barrier diodes. Rd according to the present embodiment is the device resistance of the two Schottky barrier diodes. Also, power efficiency can be found from the reflection coefficient herein, and the power efficiency can be found by $1-\Gamma^2$. Therefore, from the above expression, power efficiency can be compared in the case of using one Schottky barrier diode and in the case of using two Schottky barrier diodes as with the present embodiment.

FIG. 11 is a diagram comparing a configuration using one Schottky barrier diode with the present invention. The power efficiency increased from 28% in the case of one Schottky barrier diode to 48% in the present example.

Also, the cutoff frequency is 2 THz, both for the comparative example and the present invention. From this diagram, with the configuration of the present embodiment, the cutoff frequency is unchanged from the comparative example, but the power efficiency can be increased, i.e. the signal strength relating to electrical field strength of the electromagnetic wave (oscillating electrical field) obtained by the detector 4 can be increased, whereby SN (Signal/Noise) ratio can be increased compared to the comparative example.

The detector 4 according to the present embodiment is connected to a mixer unit 202, high-frequency power source 201, and a current measurement unit (measuring unit) 203, via a read line 200. The electromagnetic wave (oscillating electrical field) received at the antenna 100 causes high-frequency current to flow at the detecting device 3. The high-frequency current is mixed with the high-frequency current applied from the high-frequency power source 201 at the mixer unit 202, and the mixed current is measured at the current measurement unit (measuring unit) 203.

Note that an arrangement may be made wherein mixer unit 202 and high-frequency power source 201 are omitted, with the read line 200 being directly connected to the current measurement unit 203. Also, bias voltage may be applied to the read line 200 by an unshown voltage applying unit, thereby setting diode device operating point voltage. For example, with a configuration using the Schottky barrier diode according to the present embodiment, application of bias voltage around 0 V yields high sensitivity. Also, optimal bias voltage is also dependent on the electrode material of the strip conductor 103 and so forth, so forward bias of around 0.1 V is optimal with electrode materials having a relatively low work function such as Ti and Al, and forward bias of around 0.3 to 0.5 V is optimal with electrode materials having a relatively low work function such as Pt and Pd.

Figure 6:
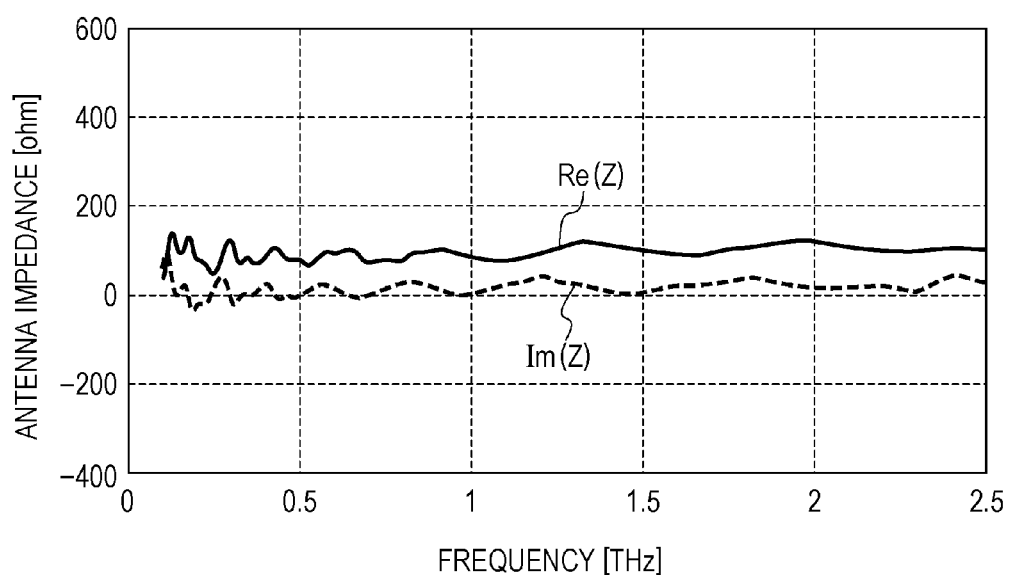
FIG. 6 is a diagram illustrating the impedance of an antenna according to the third embodiment.

FIG. 6 is a diagram illustrating the results of impedance properties of the antenna 100, obtained by performing a simulation with a high-frequency total-field simulator HFSS v12 (manufactured by Ansoft). The antenna 100 according to the present embodiment is a self-complementary antenna, with impedance of 188Ω. Further, effects of the permittivity $\epsilon_r$ of the Si substrate result in $188\Omega/\sqrt{(1+\epsilon_r)/2}$ to 80Ω, which is relatively low-impedance.

Figure 7A:
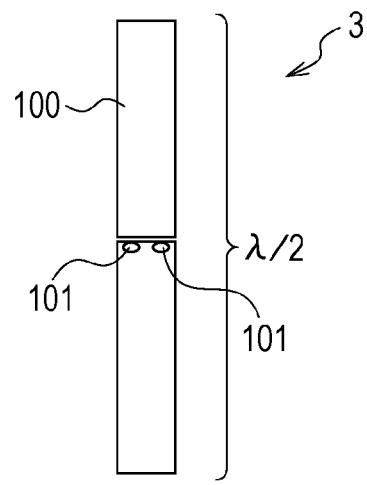
FIGS. 7A through 7C are diagrams illustrating modification examples of the antenna according to the third embodiment.
Figure 7B:
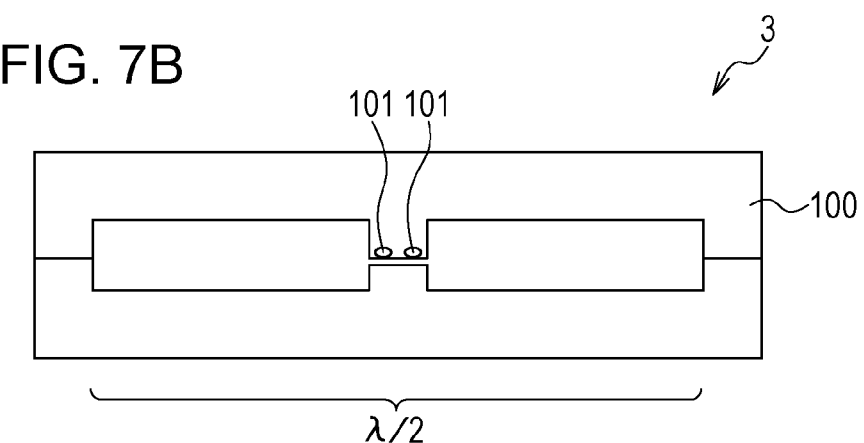
Figure 7C:
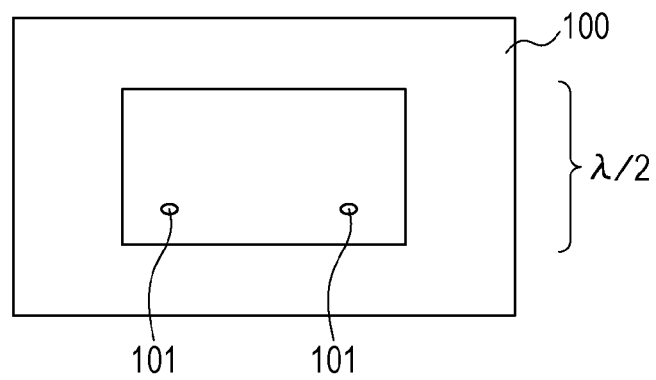

Note that the present embodiment is not restricted to the antenna described so far, and that various types of antennas may be used. FIGS. 7A through 7C are diagrams illustrating receiving antennas applicable to the present embodiment. As illustrated here, log-periodic antennas and spiral antennas are effective with detecting devices capable of detecting electromagnetic waves with extremely broad frequency bands. Slot antennas and dipole antennas having resonant frequency properties are effective as detecting devices restricting frequency band of which reception is desired. Of course, the present embodiment is not restricted to dipole antennas, and resonant patch antennas and the like may be used as well.

Fourth Embodiment

A feature of the detector according to the present embodiment is using a stereo antenna and a waveguide. Other configurations are the same as with the third embodiment, so description thereof will be omitted.

Figure 8A:
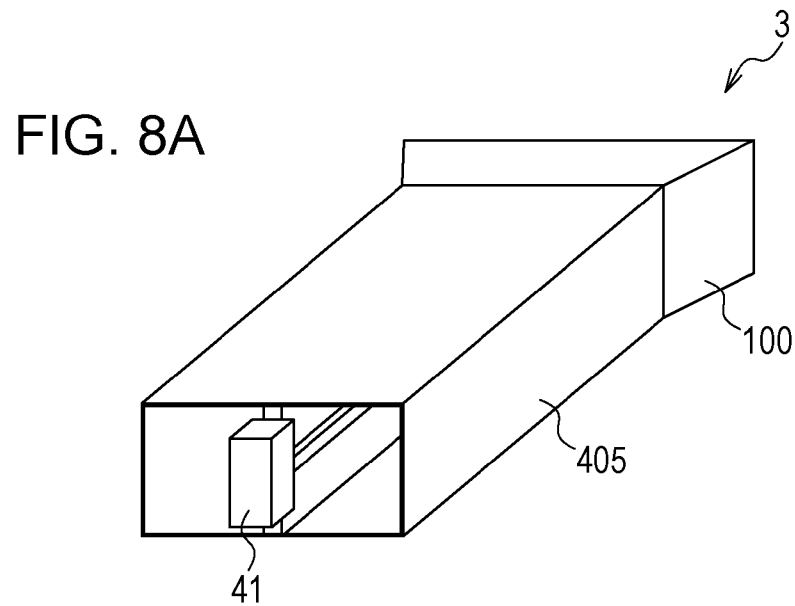
FIG. 8A is a perspective diagram illustrating a schematic configuration of a detecting device according to a fourth embodiment.
Figure 8B:
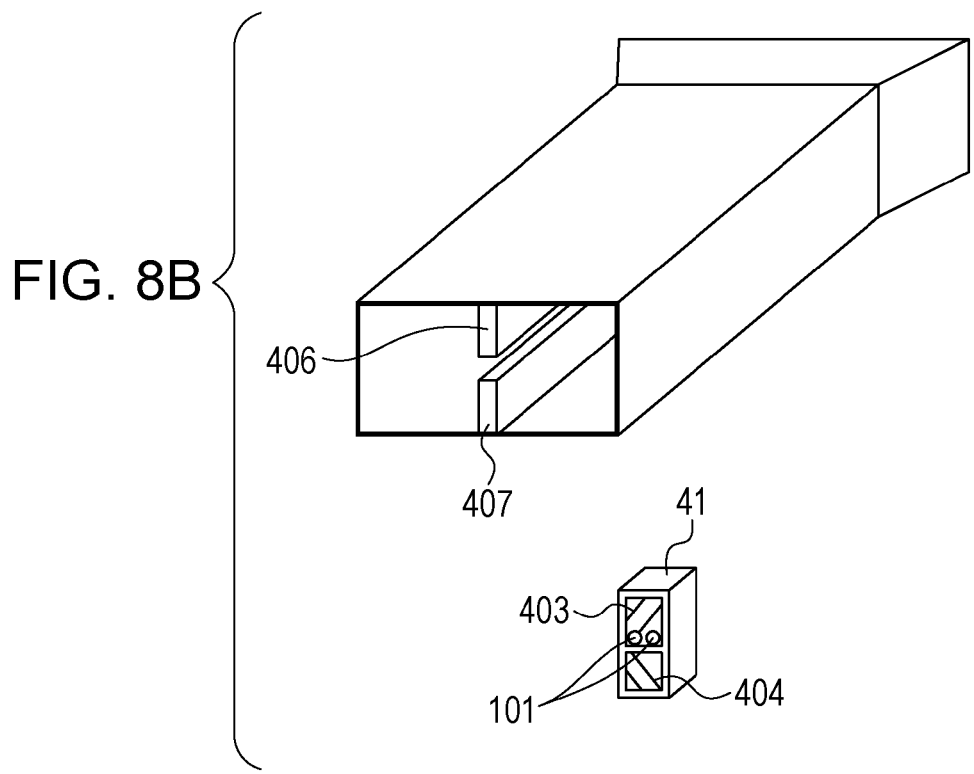
FIG. 8B is an exploded perspective diagram illustrating the detecting device and a semiconductor chip according to the fourth embodiment.

FIG. 8A is a perspective view illustrating a detecting device according to the present embodiment. FIG. 8B is a diagram with the detecting device according to the present embodiment and semiconductor chip disassembled.

With the present embodiment, a planar doped barrier diode 101 (hereinafter, PDBD) is used as a semiconductor rectifying device. Also, the arrangement includes a horn antenna 100 and a double-bridge waveguide 405 as a transmission line. Further, the detecting device 3 according to the present embodiment is arranged such that a semiconductor chip 41 includes a PDBD, so that the stereo antenna is mounted with a PDBD.

The horn antenna 100 is advantageous in that it has excellent wideband properties, and also has good directivity. The double bridge waveguide 405 is used to guide the electromagnetic waves to the semiconductor chip. The traveling-wave antenna 100 according to the present embodiment is arranged to receive between 30 GHz to 0.1 THz. The double-bridge waveguide is 3.5 mm×7.0 mm at the smallest portion, which is the near side in FIGS. 8A and 8B, and each side is fourfold in length at the widest portion, which is the opening at the far side. Ridges 406 and 407 extend from the top and bottom directions in FIGS. 8A and 8B, with the semiconductor chip 41 being soldered or the like to the ridges 406 and 407.

FIG. 8B is a diagram illustrating the parts of the detecting device before mounting. With the present embodiment, a planar barrier is formed of an n-type layer/p-type layer/n- type layer of GaAs, on a GaAs substrate, having two mesas 101 which are 5 μm in diameter. Ohmic electrodes 403 and 404 which are the two electrodes of the PDBD are electrically connected to the ridges 406 and 407. At the PDBD at the edge of the double ridge wave guide 405 thus configured, the panes of electromagnetic waves from the traveling-wave antenna 100 temporally changes, but there is no phase difference between the two PDBDs, so the two PDBDs are located at the same phase.

Figure 9:
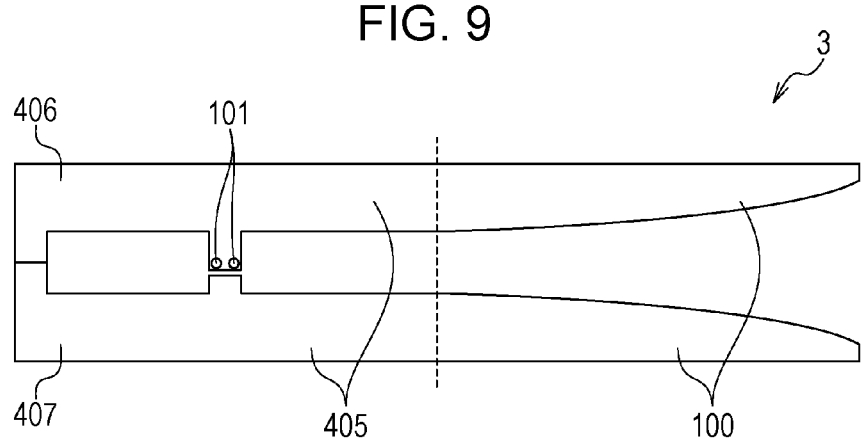
FIG. 9 is a diagram illustrating a detecting device applied to a planar antenna according to the fourth embodiment.

Note that a planar antenna and transmission line may be formed integrally. FIG. 9 is a diagram illustrating the configuration of a detecting device in a case of applying the configuration according to the present embodiment to a planar antenna. The detecting device 3 is of a configuration having a tapered slot antenna 100 and a slot line 405 (403, 404) serving as a transmission line.

Other Embodiments

FIG. 12 is a diagram schematically illustrating the configuration of an imaging apparatus. As illustrated in FIG. 12, the imaging apparatus 10 according to the present embodiment performs image pickup of images relating to objects of measurement.

The imaging apparatus 10 includes an oscillator 11 emitting electromagnetic waves of a frequency band including a part of 30 GHz to 30 THz to an object of measurement, and an image pickup unit 12 which is an image constructing unit to construct an image of an object to be measured, where two of the detecting device 3 of the above embodiments are arrayed, so as to construct an image of the object of measurement based on information relating to electromagnetic waves which have transmitted and reflected off of the object of measurement, detected by the multiple detecting devices. Also included is a power source 13 to apply voltage to the oscillator 11.

The imaging apparatus 10 emits terahertz waves generated at the oscillator 11 to the object of measurement, and detects transmitting waves and reflected waves thereafter at the detecting devices 3. At this time, physical property information such as absorption spectrum and refractive index of the object to be measured is obtained from signals relating to the field intensity (field distribution) of the terahertz waves detected at the detecting devices 3. Also, constructing an image of the object of measurement from the obtained physical property information allows the physical property information of the object of measurement to be visualized.

Note that detecting devices with different antenna lengths may be disposed so as to realize an imaging apparatus corresponding to different frequencies. Also, arraying detecting devices with different antenna orientations also realizes imaging apparatus corresponding to different polarizations.

Also, the present invention may be applied to a conventionally-used tomography apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-009335 filed Jan. 19, 2012, which is hereby incorporated by reference herein in its entirety.

What is claimed is:

1. A detecting device which detects electromagnetic waves, the detecting device comprising:

an antenna configured to receive electromagnetic waves; and a plurality of semiconductor rectifying devices serially connected to the antenna, and connected in parallel to each other such that the polarity is aligned, wherein the plurality of semiconductor rectifying devices are in contact with the antenna or connected to the antenna via a transmission line to rectify electromagnetic waves received by the antenna and transmitted, directly or via the transmission line, to the plurality of semiconductor rectifying devices, and wherein the plurality of semiconductor rectifying devices are each disposed at positions where the phase of electromagnetic waves propagated from the antenna is substantially the same phase.

2. The detecting device according to claim 1, wherein the plurality of semiconductor rectifying devices are disposed in parallel to the same wave front of the electromagnetic waves propagated from the antenna.

3. The detecting device according to claim 1, wherein at least one conductor making up the antenna and the semiconductor rectifying devices are electrically serially connected via a semiconductor layer.

4. The detecting device according to claim 1, wherein the antenna is configured of a pair of conductors, with the plurality of semiconductor rectifying devices being juxtaposed in contact with one of the pair.

5. The detecting device according to claim 4, wherein the pair of antennas is made up of two conductors which are disposed on a substrate in a non-contacting state.

6. The detecting device according to claim 1, wherein the antenna has formed thereto a salient portion, with the salient portion being situated between the plurality of semiconductor rectifying devices.

7. The detecting device according to claim 1, wherein the transmission line is connected to the antenna and the plurality of semiconductor rectifying devices.

8. The detecting device according to claim 1, wherein the plurality of semiconductor rectifying devices are disposed at a position where the absolute value of phase difference of the electromagnetic waves propagated from the antenna is 0 or greater and $\pi/16$ or smaller.

9. The detecting device according to claim 8, wherein the plurality of semiconductor rectifying devices are disposed at a position where the absolute value of phase difference of the electromagnetic waves propagated from the antenna is 0 or greater and $\pi/32$ or smaller.

10. The detecting device according to claim 1, wherein, the plurality of semiconductor rectifying devices are equal in the area of a cross-section perpendicular to the direction in which current flows at a junction making up the semiconductor rectifying devices.

11. The detecting device according to claim 10, wherein the area of the junction is 10 $\mu m^2$ or smaller.

12. The detecting device according to claim 10, wherein the junction of the each of the plurality of semiconductor rectifying devices is a cylindrical shape surrounded by a dielectric.

13. The detecting device according to claim 1, wherein the plurality of semiconductor rectifying devices are formed using silicon.

14. The detecting device according to claim 13, wherein the plurality of semiconductor rectifying devices are Schottky barrier diodes or planar doped barrier diodes.

15. The detecting device according to claim 1, wherein the plurality of semiconductor rectifying devices are formed using a compound semiconductor material.

16. The detecting device according to claim 15, wherein the plurality of semiconductor rectifying devices are formed using a Group III-V semiconductor material.

17. The detecting device according to claim 1, the detecting device detecting electromagnetic waves of a frequency band including a part of 30 GHz to 30 THz.

18. The detecting device according to claim 1, wherein at least two of the plurality of semiconductor rectifying devices are each disposed at positions where the phase of electromagnetic waves propagated from the antenna is substantially the same phase.

19. A detector to detect electromagnetic waves, the detector comprising:
a detecting device which detects electromagnetic waves, the detecting device comprising:
an antenna configured to receive electromagnetic waves; and
a plurality of semiconductor rectifying devices serially connected to the antenna, and connected in parallel to each other such that the polarity is aligned,
wherein the plurality of semiconductor rectifying devices are in contact with the antenna or connected to the antenna via a transmission line to rectify electromagnetic waves received by the antenna and transmitted, directly or via the transmission line, to the plurality of semiconductor rectifying devices, and
wherein the plurality of semiconductor rectifying devices are each disposed at positions where the phase of electromagnetic waves propagated from the antenna is substantially the same phase; and
a measuring unit configured to measure an electric field at the antenna.

20. An imaging apparatus to perform image pickup of an object of measurement using electromagnetic waves, the imaging apparatus comprising:
an oscillator configured to oscillate electromagnetic waves of a frequency band including a part of 30 GHz to 30 THz;
a detector to detect electromagnetic waves, the detector comprising:
a detecting device which detects electromagnetic waves, the detecting device comprising:
an antenna configured to receive electromagnetic waves; and
a plurality of semiconductor rectifying devices serially connected to the antenna, and connected in parallel to each other such that the polarity is aligned,
wherein the plurality of semiconductor rectifying devices are in contact with the antenna or connected to the antenna via a transmission line to rectify electromagnetic waves received by the antenna and transmitted, directly or via the transmission line, to the plurality of semiconductor rectifying devices, and
wherein the plurality of semiconductor rectifying devices are each disposed at positions where the phase of electromagnetic waves propagated from the antenna is substantially the same phase; and
a measuring unit configured to measure an electric field at the antenna; and
an image constructing unit configured to construct an image relating to the object of measurement, based on electromagnetic waves detected by the detector.

\* \* \* \* \*